United States Patent [19]

Shonk

[11] Patent Number: 4,699,157

[45] Date of Patent: Oct. 13, 1987

[54] PACING CATHETER AND METHOD OF MAKING SAME

[75] Inventor: Robert S. Shonk, Glen Rock, N.J.

[73] Assignee: Electro-Catheter Corporation, Rahway, N.J.

[21] Appl. No.: 769,933

[22] Filed: Aug. 27, 1985

[51] Int. Cl.[4] .............................................. A61N 1/04
[52] U.S. Cl. .................................. 128/786; 128/784; 128/419 P
[58] Field of Search ............... 128/639, 642, 656, 657, 128/658, 419 P, 419 S, 772, 774, 783, 784, 786

[56] References Cited

U.S. PATENT DOCUMENTS

| | | | |
|---|---|---|---|
| 3,485,234 | 12/1969 | Stevens | 128/657 |
| 3,769,984 | 11/1973 | Muench | 128/786 |
| 3,893,461 | 7/1975 | Preston | 128/419 P |
| 3,903,896 | 9/1975 | Harmjanz | 128/419 P |
| 3,915,174 | 10/1975 | Preston | 128/786 |
| 3,977,411 | 8/1976 | Hughes, Jr. et al. | 128/786 |
| 4,010,755 | 3/1977 | Preston | 128/419 P |
| 4,149,542 | 4/1979 | Thoren | 128/786 |

OTHER PUBLICATIONS

IBM Technical Disclosure Bulletin, "Body Tissue Transducer", Johnston et al, Jan. 1964, vol. 6, No. 8, pp. 13-14.

Journal of Medical Engineering & Technology, Gosling et al, "A Hand-Held Probe for Recording Epicardial Signals", Nov. 1979, p. 299.

Primary Examiner—Edward M. Coven
Attorney, Agent, or Firm—Philip Young

[57] ABSTRACT

A pacing catheter having improved torque control properties, including a polymeric tube having an electrically conductive torque member passing through the tube center. The torque member is tapered near the distal end where it is secured to a cup-shaped electrode adapted to fit over the distal end of the polymeric tube. The space between the polymeric tube and the torque member is filled with a polymeric or elastomeric material in fluid form such that a solid, but flexible, polymeric composition is formed which adheres to both the inside of the polymeric tube and the outside of the torque member. The solidified liquid polymeric material allows rotation force applied anywhere along the hollow outer tube to be directly transmitted to the central torque member.

16 Claims, 9 Drawing Figures

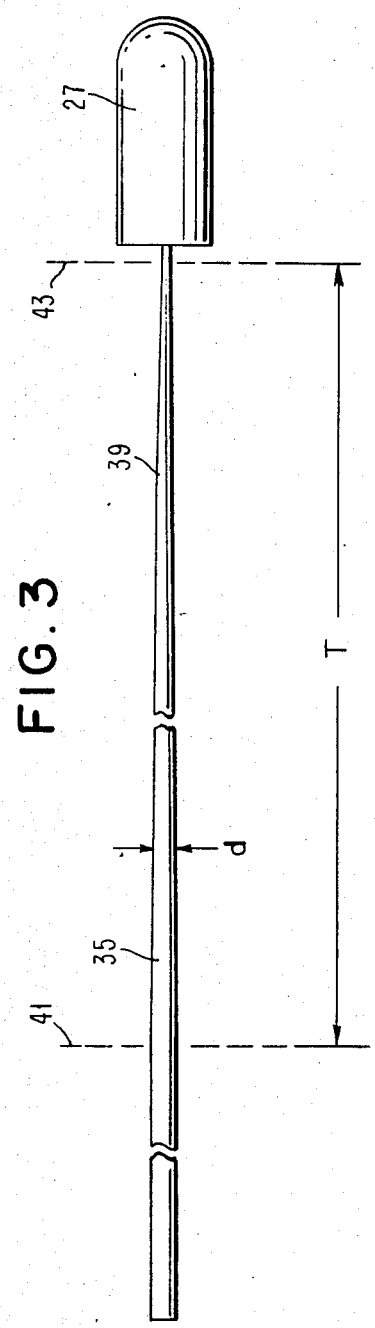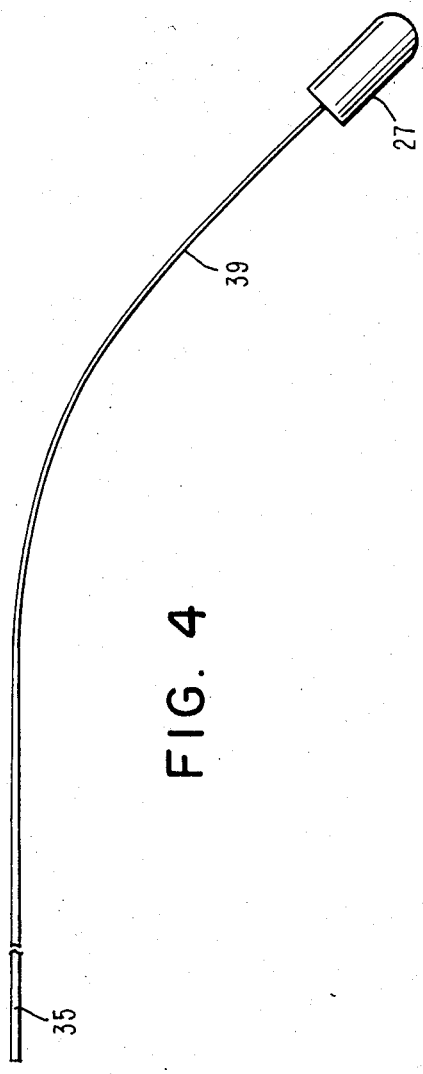

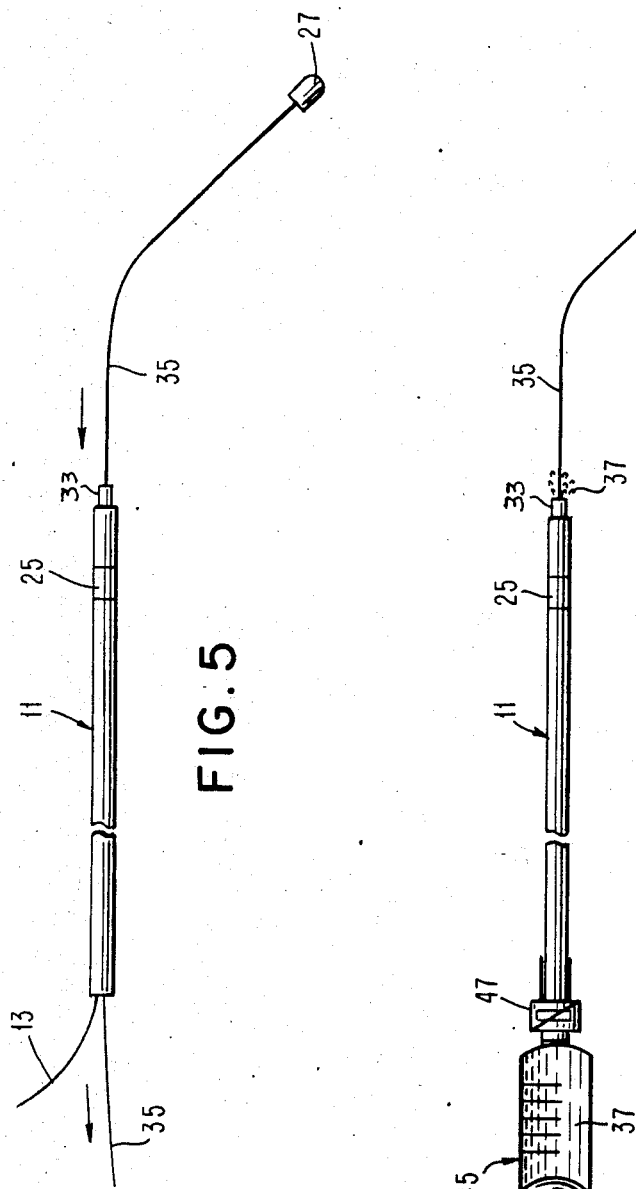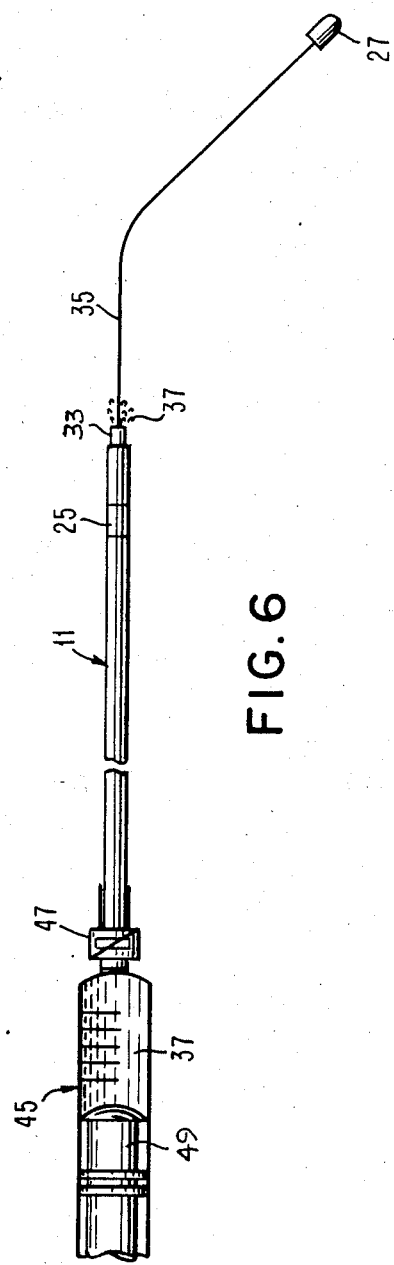

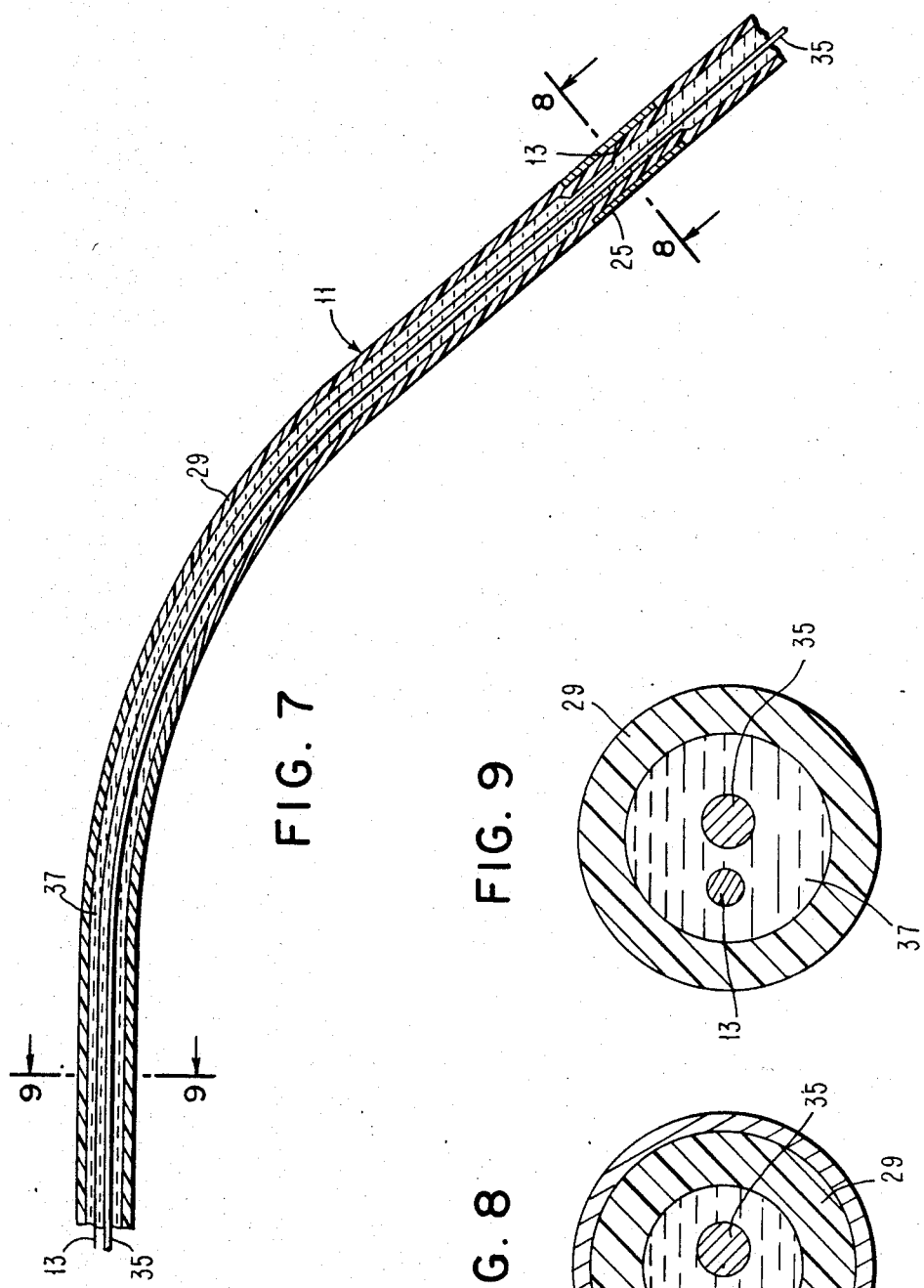

PACING CATHETER AND METHOD OF MAKING SAME

BACKGROUND OF THE INVENTION

1. Field of the Invention

This invention relates to linearly extended devices suitable for insertion into living bodies via blood vessels and the like, and more particularly to transvenous catheters for conducting electrical pulses between the exterior of the body and the heart.

2. Description of the Prior Art

Conventional heart catheter devices comprise electrical pulse conducting elements in the form of elongated flexible members of some suitable polymeric material. Suitable flexible conductors are disposed within the insulating polymeric material to conduct electrical impulses between an electrical impulse generating means connected to the near, or proximal, end of the catheter and tissue contacting electrodes disposed at the far, or distal, end of the catheter. The electrodes are positioned on or partially embedded in the surface of the elongated catheter element. The catheter may be either unipolar, i.e., with one electrical conductor passing through it, or bipolar with two electrical conductors passing through it. There may also be an additional tension member within the elongated catheter element to provide longitudinal strength and integrity. Alternatively, a conductor or conductors passing through the catheter may provide the catheter with the requisite longitudinal strength under tension. The tension member or conductors may also provide torsional rigidity to the catheter over its length so it may be rotated by torsional force supplied at the proximal end. This enables the distal end to be rotated for better guidance as it is threaded through blood vessels and the heart chambers into final position in the lumen or interior of the heart. Catheters designed for such rotation are usually provided with a somewhat offset or bent distal end so that when the catheter is rotated, the offset end facilitates guidance of the catheter in the desired direction through the blood vessels and into the heart chambers. The ability to rotate a catheter probe is often referred to as "torque control". Also, it is desirable for the catheter probe to have a very flexible distal tip so it can be directed by the flow of blood in the venous system, such directional ability sometimes being referred to as being "floated" through the veneous system. The soft flexible distal tip of the probe also prevents trauma to the surrounding body tissues as the catheter probe is passed through the blood vessels.

Modern catheters have been conventionally formed of a polymeric material which is inert or substantially inert to body fluids. Silicon rubber, polyvinylchloride, polyethylene or polyurethane may, for example, be used. The polymeric material can be extruded directly about the conductors and, if one is used, about the central tension member. Such catheters have a substantially solid cross section. Some early catheter probes were constructed of polymeric tubes within which the conductors were more or less loosely gathered. Tubular catheters having the conductors embedded in the wall of the tubing about a central lumen or channel have also been used.

Various electrodes may be used on the surface of the catheters to provide electrical contact between the interior of the heart or other intravenous structures and the conductors within the catheter. Such electrodes may be formed, for example, from rings and cups of various conductive materials resistant to body fluids. The conductors in the catheter are formed usually from thin braided or twisted, highly flexible, small diameter filaments, for example, tantalum, platinum, silver, stainless steel or other metallic materials substantially inert to body fluids. Bipolar catheters may have their proximal and distal electrodes either relatively closely or widely spaced from each other along the longitudinal extent of the catheter. Both unipolar and bipolar catheters may be provided with one or several electrodes connected to each conductor. The polymeric material of the catheter is selected or formulated and, if necessary, treated, to provide a soft, highly flexible composition in order to prevent trauma to surrounding tissues and allow easy threading and "floating" through the venous vessels into the heart chambers. Additionally the catheter, in order to provide minimum interference with the flow of blood through the venous vessels and irritation of such vessels and the heart itself, should have a very small diameter as well known to those skilled in the art. The following patents are exemplary of the state of the art summarized above.

U.S. Pat. No. 3,769,984 to Muench discloses a bipolar catheter incorporating either a cup shaped or ring type electrode at the distal end plus a ring electrode proximal thereto. The catheter may include an axial lumen which may accomodate additional apparatus including a guide wire during venous insertion.

U.S. Pat. No. 3,893,461 to Preston discloses a bipolar catheter in which the proximal electrode is significantly spaced from the distal electrode and has a surface area an order of magnitude greater than that of the distal electrode, such electrodes being embedded in a plastic member characterized as having a generally tubular form.

U.S. Pat. No. 3,903,896 to Harmjanz discloses a catheter formed from a solid core of plastic incorporating a central structural core which absorbs tensile forces. Conductors on both sides of the structural core may be contacted by compression type sleeve electrodes clamped to the surface of the catheter after removal of surface polymer material over either of the conductors.

U.S. Pat. No. 3,915,174 to Preston discloses a bipolar catheter having substantially spaced surface electrodes embedded in a plastic catheter body characterized as having a generally tubular form.

U.S. Pat. No. 3,977,411 to Hughs et al discloses a cardiac pacer system incorporating a catheter having electrodes with large and small surface areas for respectively detecting cardiac electrical potentials and electrically stimulating the cardiac tissues. The electrodes may be connected to a single or multiple electrical conductors or leads embedded in a suitable body compatible, flexible non-conductive material.

Finally, U.S. Pat. No. 4,010,755 to Preston discloses a bipolar catheter having conductors embedded in a substantially inert non-conducting casing. Two distal electrodes are used, both connected to the same conductor, and it is disclosed that the catheter could operate in a unipolar mode.

As indicated above in the known catheters, it is highly desirable that a catheter have "torque control", i.e., the ability to be rotated in a controlled manner to facilitate guidance through the venous system and correct placement in the heart chambers. Two principal methods are presently known to produce the desired properties.

One method is to embed a woven mesh material in the wall of a flexible polymeric tubing or the like. The woven mesh may be either metallic material such as stainless steel or the like or a polymeric material such as a polyester. Catheters constructed in this manner have torque control properties and may usually be rotated from any portion of the catheter, sufficient transverse rigidity being provided by the embedded mesh material to allow rotation by transversely applied torsional forces along the body of the catheter probe. This construction is expensive, however, and the rigidity of the catheter body tends to decrease flexibility and presents a possible source of trauma and irritation to adjacent tissues.

A further known method provides a single stiff wire tapered toward the end of the catheter and secured at the distal end to an end cap electrode and at the proximal end to the catheter body. This type of torque controlled catheter has excellent control when the proximal end is rotated, but the ability to transmit rotational forces applied elsewhere along the body of the catheter, for example, by manual grasping or gripping, is severly limited by the softness of the polymeric body material of the catheter.

SUMMARY OF THE INVENTION

In view of the above, it is an object of the present invention to provide a torque control type heart catheter exhibiting excellent rotational control with superior softness and flexibility to prevent damage to adjacent tissues and to facilitate efficient guidance through the venous system for placement in the heart chambers. It is a further object of the invention to provide an efficient and cost effective method of making a torque controlled catheter.

These and other objects are achieved by the present invention which provides a catheter constructed in the form of a hollow polymeric tube having a torque member passing through the interior thereof, preferably along the central axis and having a solidified liquid polymeric or elastomeric material disposed in close securing relationship between the torque member and the outer polymeric tube. The solidified liquid polymeric material allows rotational force applied anywhere along the hollow outer tube or envelope of the catheter body to be directly transmitted to the central torque control member even though the filling material is flexible and soft. The outer envelope provides circumferential strength and constructional rigidity when transverse rotational forces are applied to the surface, but is sufficiently soft and flexible to prevent trauma and irritation to adjacent tissues. The construction is also easier and less expensive to make than prior mesh reinforced constructions.

The torque controlled catheter of the present invention may be made by providing a tubular member having a length and outside diameter substantiably equal to the dimensions of the catheter probe to be constructed. A torque member having a diameter substantially smaller than the inside diameter of the tubing is then placed in the tubing by threading the torque member through said tubing from one end. The torque member is preferably tapered from one end to the other, particularly near the distal end. The distal end of the torque member is also preferably secured to a cup-shaped electrode adapted to fit over the distal end of the polymeric tube. After the torque member, which is preferably an electrical conductor, is threaded through the polymeric tube or jacket, the space between the two is filled with a polymeric or elastomeric composition in fluid form, after which such composition is allowed to harden by curing, vulcanizing, solidifying from a liquid, sintering, or by oher suitable chemical or physical action so that a solid, but flexible, polymeric composition is formed which adheres to both the inside of the tubing and the outside of the torque member. The torque member is preferably electrically conductive so that it serves not only as a torque member, but as the internal electrical connection between the cup shaped electrode to which it is connected and a heart monitoring or pacing apparatus connected to the other end. A second electrode and conductor are also preferably used in the catheter probe of the invention. The polymeric or elastomeric material must be adhesive to the outer tubing and to the torque member to allow rotation of the catheter along its length and is preferably adhesive also to the rear of the cup shaped electrode to improve the rotatability of the catheter. The catheter will usually also be provided with an angled or bent end to improve the torque control.

BRIEF DESCRIPTION OF THE DRAWINGS

FIG. 3 is a side view of the distal cup shaped electrode with a tapered torque member attached thereto prior to insertion into the catheter tube.

FIG. 4 is a side view of the distal cup-shaped electrode with a typical torque member attached thereto and bent into shape just prior to insertion into the catheter.

FIG. 5 is an overall view of the catheter with the torque member and cup-shaped electrode being inserted into the catheter body.

FIG. 6 shows the catheter during manufacture when a fluid material injection device is coupled to a catheter end;

FIG. 7 is an enlarged longitudinal section of a portion of the completed catheter with the distal end bent into position and the liquid polymer or elastomer material filled in the space between the inside of the tubing and the outside of the torque member.

FIGS. 8 and 9 are cross sections of the catheter probe taken through sections 8—8 and 9—9, respectively, shown in both FIGS. 1 and 7.

DESCRIPTION OF THE PREFERRED EMBODIMENTS

Figure 1:
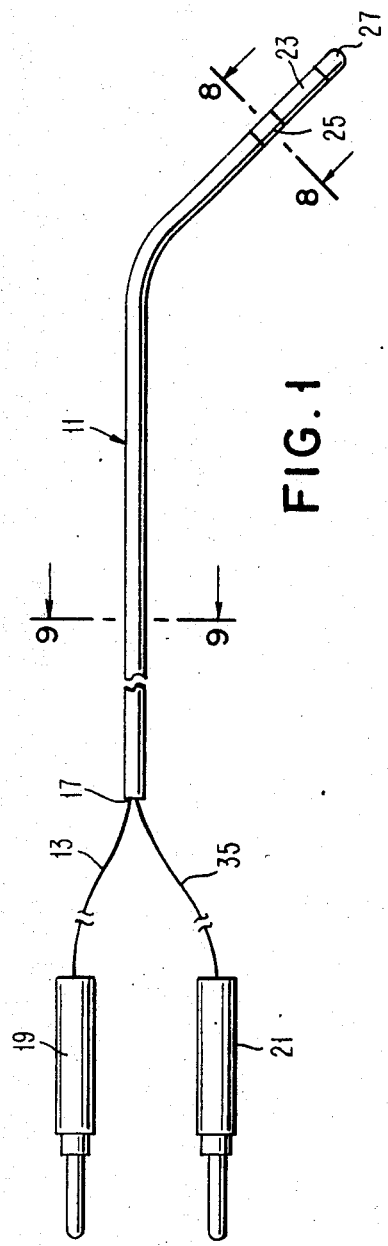
FIG. 1 is a side view of a typical catheter constructed in accordance with the invention.

In FIG. 1 there is shown an overall side view of a preferred embodiment of the invention including a polymeric tubular catheter body 11 and two electrical leads 13 and 35 extending from the proximal end 17. Pins 19 and 21 are supplied at the ends of the leads for connecting to a heart pacer apparatus which may be of known construction and is therefore not shown. The distal end 23 of the catheter is deviated or bent at a shallow angle from the direction of the remainder of the catheter and includes a proximal sleeve type electrode 25 and a distal cup-shaped electrode 27 at the extreme distal end or terminal end of the catheter.

Figure 2:
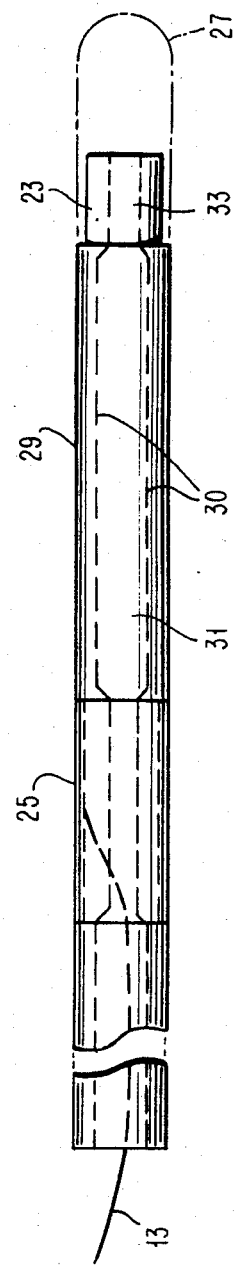
FIG. 2 is a side view partially in phantom of the distal end of the catheter prior to the application of the torque member within the catheter.

FIG. 2 is an enlargement of the distal end 23 of a portion of the catheter probe assembly prior to completion. FIG. 2 shows in phantom by dashed lines 30 the inside surface of outer polymeric tubing 29 from which the catheter probe is constructed plus a central opening or lumen 31 of the tube through which the wire lead 13 from proximal electrode 25 passes. Suitable polymeric materials for the outer tubing include silicon rubber, polyvinychloride, polyethylene and polyurethane. The extreme distal end 23 or terminal end of the catheter is preformed at 33 to receive the cup-shaped electrode 27 shown in FIG. 1.

FIG. 3 shows the torque member 35 which in the embodiment shown is an extension of electrical lead 35 shown in FIG. 1, attached to the cup-shaped distal electrode 27 prior to assembly with the remainder of the catheter elements. It can be seen that the torque member 35 is tapered along its length toward the electrode, particularly in the section nearest the electrode. This facilitates flexibility of the distal end of the catheter in particular. The torque member 35 will preferably be tapered as shown substantially from end to end, but may if desired be tapered only at the distal end 39 toward the cup-shaped fitting. In the latter case illustrated in FIG. 3, the torque member 35 is tapered at its distal end 39 over a length T extending between the broken lines 41 and 43. The tapered end T of torque member 35 may, for example, be four or five inches in length and have a diameter d varying from, for example, 0.015 or 0.020 inches at its largest point 41 down to 0.005 inches at its narrowest point 43. The use of the tapered torque member 35 provides less firmness and more "give" at the catheter distal end as the torque member is advanced through the veins, thereby avoiding traumatic effects of the catheter on the body system.

The inner torque member 35 can comprise any material or composition that is more torsion resistant than the outer flexible tube 29. While the preferred embodiment of torque member 35 is tempered stainless steel wire, braided metal cable or metal polymer composite cable, or a filled polymer monofilament, such as glass reinforced nylon, can also be employed. Other torque member materials include, for example, tantalum, platinum, or a strong polymeric material. It is preferred to form the torque member from a conductor material so it may also serve as the electrical connection of the cup-shaped electrode. However, a separate conductor could be used in addition to the torque member.

In making the catheter of the invention, the torque member 35 is threaded through the tubular jacket or polymeric tube 29 and the cup-shaped electrode 27 is drawn up against and over the preformed end 33 of the tubing 29 as shown in FIGS. 2 and 5. Preferably, the end of the torque member 35 is first bent as seen in FIGS. 4 and 5 so that when the straight tube 29 is drawn over the bent end of the torque member as shown in FIGS. 1 and 7, the distal end 23 of the catheter is bent into a final shape as seen in FIG. 1 in which the distal end is angled to one side to facilitate threading of the final catheter element through the venous vessels and into the heart chambers.

After the tubing 29 and torque member 35 are assembled together, the space between the inside of the tubing 29 and the outside of the torque member is filled with a liquid polymer or elastomer which is allowed to solidify. This solidified polymer is shown in FIGS. 7, 8 and 9 as a central polymer 37 which surrounds the torque member 35 as well as the other electrode wire 13. Suitable polymeric filling materials 37 include those changing from liquid to solid by vulcanization, crosslinking, or curing with heat or at room temperature, such as silicone rubber, depolymerized natural rubber, polyurethane rubber and epoxy. Polymeric filling material 37 may also include those changing from liquid to solid by gelling with heat, such as polyvinyl chloride plastisol, polyvinylacetate plastisol, or combinations thereof. Other suitable polymeric filling materials 37 include those changing from liquid to solid by cooling, such as low molecular weight polyethylene wax, and polyvinylacetate hot melt adhesive. Also, the polymeric filling material 37 may include those changing from liquid to solid state by drying, such as any polymeric material dissolved in solvent such as polyvinylchloride in tetrahydrofuran, and materials changing from fluid state, i.e., powder to solid state by sintering with heat, such as plasticized polyvinylchloride powder.

It is to be understood that the term solidify is used generally to refer to any chemical or physical process which solidifies or hardens the polymer such as actual solidification of a melted polymer, curing, vulcanizing, gelling, drying, i.e., removal or vaporization of solvents, and all types of cross linking and the like. Suitable polymers are listed above and include polymers formulated to remain flexible and soft, yet when encased in the outer jacket or tubing 29, present a firm construction which will enable the force exerted upon the surface of the tubing to be transferred to the torque member. The central polymer or elastomer referred to generally herein as a polymeric material must also be adhesive to the torque member 35 and to the tube 29 and have when solidified sufficient shear strength to enable rotation of either the torque member or the tubular jacket to rotate the other member, i.e., either the torque member or the tubular jacket, within an intrabody environment. The polymeric filling material when solidified is intrinsically softer and more flexible than the polymeric material of the tubular outer jacket.

The fluid or liquid polymeric filling material may be injected into the space between the plastic jacket 29 and the torque member 35 in any suitable manner such as by (a) pouring the material into the outer tubing 29 from either end, (b) positive pressure injection into either open end using a coupling or fitting which mates to the end opening and is removed after filling, (c) applying a vacuum to one open end and placing the other open end into the liquid material, or (d) inserting a needle through the side wall of the tube and injecting the material such that the side wall closes upon removal of the needle. In the latter method, partial filling can be accomplished and the filling can be done at multiple sites along the tube, not shown.

The preferred method is accomplished with the fluid injector device 45 which is attached by a nozzle coupling 47 to the end of the catheter body 11, as shown in FIG. 6. Here, the inner torque wire member 35 is inserted through the outer tube 29 with cup shaped electrode 27 already attached, and the cup shaped electrode 27 is brought to the vicinity of formed distal end 33. The open proximal end of tubing 11 is attached to nozzle coupling 47 and the tube filled with the liquid material 37 by pushing a plunger 49 under pressure until it exits the distal end 33 of tubing 11 as shown. Then, the tubing 11 is removed from the nozzle coupling 47 and cup electrode 27 brought into contact with the preformed end of tube 33.

The rotation force applied to the outer tube 29 is transferred to the solidified polymer either by adhesion of the polymer to the inner tube surface, by friction between the two surfaces, or by physical interference if the inner tube surface is textured with a resultant mating texture of the solidified polymer. The force is transferred in turn to the inner torque member by the same mechanisms.

In the preferred embodiment showing the initially fluid polymer filling material 37 35 in FIGS. 7, 8 and 9, the force is transferred by adhesion of the contact surfaces i.e. the inner surfaces of the outer tube 29 and the outer surface of the torque member 35, with the solidified polymeric material 37.

FIG. 7 shows an enlargement of a portion of the catheter with the polymeric material 37 filled in the space between the inside of the tubing 29 and the torque member 35. FIG. 8 is a sectional view taken through the proximal electrode 25, while FIG. 9 is a sectional view taken through the tubing 29 at section 9—9. The outside diameter of electrode 25 is the same as the outside diameter of tubing 29 at those points, such as section 9—9, where the electrodes are not located.

Surprisingly, when constructed in the manner of the invention, the catheter remains soft and pliable even though sufficient firmness is supplied to rotate the catheter by surface pressure along its length rather than only at the proximal end. The confinement of the soft flexible polymeric material within the jacket having a different firmness allows both firmness and flexibility. In this manner, the choice of a flexible elastomeric filling material does not alter the overall flexibility of the combined construction of the catheter probe.

It will be understood that while the present invention has been described with considerable specificity, is to be broadly construed within the bounds of the appended claims. Other embodiments may be successfully made with, for example, multiple lumens or openings in the polymeric jacket, one or more of which are filled with solidified polymer and the lumen or lumens may be either uniformly filled with plastic or discontinuously filled so long as sufficient plastic is injected to provide a structual web at effective intervals between the torque member and the jacket to bind the two together with sufficient rotational rigidity to accomplish the desired aim of the invention. The polymer material will still perform satisfactorily if it is discontinuous although not as well as if filled fully. In this case, the torque force would have to be transferred to the nearest site where the inner material is present.

It will be recognized furthermore that the invention can be used with various catheter arrangements, such as either unipolar or bipolar devices and each polarity may be applied to single or plural electrodes spaced at various distances from each other.

What is claimed is:

1. A longitudinally extended catheter body exhibiting improved torque control comprising:
   (a) an outer polymeric jacket made of at least one hollow tube formed from a first polymeric material which provides circumferential strength and rigidity;
   (b) a single wire torque member extending longitudinally within said polymeric jacket, said torque member being electrically conductive and extending substantially along the longitudinal axis of said catheter body, said wire torque member having a diameter substantially smaller than the inside diameter of said outer polymeric jacket and being capable of transmitting torque forces along its length;
   (c) distal electrode means attached to an end of said wire torque member; and
   (d) a second polymeric material in the form of a solidified filling material enveloping said torque member within and substantially filling said outer polymeric jacket at least discontinuously along the longitudinal extent thereof, said solidified polymeric material having a different firmness from that of the polymeric jacket and having adhesive properties so that it is adherent to both the inner walls of said polymeric jacket and to said wire torque member to form an effectively rotationally rigid circumferential web therebetween;
   whereby said catheter body enables the transmission of torque forces between the outside surface of said polymeric jacket and said torque member for improved rotatability of said catheter body.

2. The catheter body of claim 1 wherein a portion of the distal end of said catheter body extends at an angle from a principal longitudinal portion of said catheter body.

3. The catheter body of claim 1 wherein said outer polymeric jacket has more than one lumen arranged with their central axes parallel to a common longitudinal axis.

4. The catheter body as recited in claim 1 additionally comprising at least one sleeve type proximal electrode positioned over the surface of said polymeric jacket and an electrically conductive wire attached to said sleeve electrode and extending through the side wall of said polymeric jacket and traversing a substantial length of said polymeric jacket.

5. The catheter body of claim 4 wherein the distal electrode is a cup-type electrode disposed at the end of the catheter body in contact with and adherent to the solidified polymeric material.

6. The catheter body of claim 5 wherein a portion of the distal end of said catheter body extends at an angle from a principal longitudinal portion of said catheter body and the proximal electrode is disposed upon the angled portion of the distal end of the catheter body.

7. The catheter of claim 6 wherein the cross section of said torque member generally tapers from the proximal to the distal ends of said catheter body.

8. The catheter body of claim 7 wherein the cross section of the outer polymeric jacket is substantially circular.

9. The catheter body as recited in claim 1, wherein said outer polymeric jacket is made from one or more of the polymeric materials taken from the class of polyvinylchloride, polyethylene, polyurethane or silicon rubber.

10. The catheter body as recited in claim 1, wherein said torque member has a diameter which tapers down towards the distal end of said catheter body adjacent to said electrode means attached at the distal end of said torque member.

11. The catheter body as recited in claim 10, wherein the diameter of said torque member is in the range of about 0.015 to 0.020 inches, and said diameter is reduced in the tapered portion near said electrode means at said distal end to a diameter of about 0.005 inches.

12. The catheter body as recited in claim 1, wherein said torque member is made of stainless steel wire.

13. The catheter body as recited in claim 1, wherein said polymeric material enveloping said torque member is taken from the class of polymers including silicone rubber, depolymerized natural rubber, polyurethane rubber, epoxy, polyvinyl chloride plastisol, polyvinylacetate plastisol, or polyethylene wax.

14. The catheter body of claim 1 wherein the solidified polymeric filling material is longitudinally continuous along the catheter body.

15. The catheter body of claim 2 wherein the solidified polymeric filling material within the outer polymeric jacket is intrinsically softer and more flexible than the polymeric jacket material.

16. A longitudinally extended catheter body exhibiting improved torque control comprising:
  (a) an outer polymeric jacket made of at least one hollow tube of a polymeric material having a circular, ring-like transverse cross-section;
  (b) a torque member extending longitudinally within said polymeric jacket, said torque member being electrically conductive and extending substantially along the longitudinal axis of said catheter body, said torque member being capable of transmitting torque forces along its length;
  (c) a cup-shaped distal electrode attached to a distal end of said torque member, the outer diameter of said cup-shaped electrode being substantially the same as the outer diameter of said outer polymeric jacket;
  (d) at least one sleeve electrode positioned over the outer surface of said polymeric jacket, wherein the catheter is bipolar by virtue of having a second electrical conductor means therein attached to said sleeve electrode;
  (e) a solidified polymeric filling material enveloping said torque member within and substantially filling said outer polymeric jacket, said solidified polymeric material being adherent to both the inner walls of said polymeric jacket and to said torque member, said solidified polymeric material being intrinsically softer and more flexible than said polymeric jacket material;

whereby said catheter body enables the transmitting of torque forces between the outside surface of said polymeric jacket and said torque member.

* * * * *